(12) United States Patent
Schrick

(10) Patent No.: US 8,715,155 B2
(45) Date of Patent: *May 6, 2014

(54) EMBRYO DEVELOPMENT AND SURVIVAL

(75) Inventor: F. Neal Schrick, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 1484 days.

This patent is subject to a terminal disclaimer.

(21) Appl. No.: 12/220,978

(22) Filed: Jul. 29, 2008

(65) Prior Publication Data

US 2008/0300450 A1 Dec. 4, 2008

Related U.S. Application Data

(63) Continuation-in-part of application No. 11/039,662, filed on Jan. 19, 2005, now Pat. No. 7,705,197.

(51) Int. Cl.
*A61B 17/435* (2006.01)
*A61D 7/00* (2006.01)

(52) U.S. Cl.
USPC .................... 600/34; 800/8; 800/15; 435/325

(58) Field of Classification Search
None
See application file for complete search history.

(56) References Cited

U.S. PATENT DOCUMENTS

| | | |
|---|---|---|
| 5,760,024 A | 6/1998 | Macnamee |
| 6,100,249 A | 8/2000 | Macnamee |
| 6,300,312 B1 | 10/2001 | Chemtob |

OTHER PUBLICATIONS

Krogenes, A., et al, "Effects of non-steroidal anti-Inflammatory drugs in the maturation and fertilization media on bovine oocytes, " Therlogenology, 40:1029-1038 (1993).
Spezia, F., et al, "Action of allopurinol and aspirin on rat whole-embryo cultures," Toxicology, 72:239-250 (1992).
Elli, "Effect of a single dose of ibuprofen lysinate before embryo transfer on pregnancy rates in cows," Reproduction, 121:151-154 (2001).
Griffen, "AL-8810: A novel prostaglandin F2a analog with selective antagonist effects at the . . . ," J. Pharmacology and Experimental Therapeutics, 290(3):1278-1284 (1999).
Hockett, "Alterations in embryo development in progestogen-supplemented cows administered prostaglandin F2a," Prostaglandins & Other Lipid Mediators, 73:227-236 (2004).

Rubinstein, "Low-dose aspirin treatment improves ovarian responsiveness, uterine and ovarian blood flow velocity, . . . ", Fertility and Sterility, 72(5):825-829 (1999).
Scenna, "Detrimental effects of prostagladin F2a on preimplantation bovine embryos," Prostaglandins & Other Lipid Mediators, 73:215-226 (2004).
Schrick, "Prostaglandin F2a appears to directly influence early embryonic survival . . . ," in Proceedings of the American Embryo Transfer Assoc., Sacramento, CA pp. 9-16 (2000).
Sharif, "Bimatoprost and its free acid are prostaglandin FP receptor agonists," European Journal of Pharmacology, 432:211-213 (2001).
Waldenstrom, "Low-dose aspirin in a short regimen as standard treatment in in vitro fertilization," Fertility and Sterility, 81(6):1560-1564 (2004).
Pugh, "Influence of prostaglandin F2a synthesis inhibitors on pregnancy rates of embryo transfer recipient . . . ", 15th Intl. Congress on Animal Reproduction (ICAR) (2004).
McNaughton, "The effect of prostaglandin inhibition on pregnancy rates of heifer embryo transfer recipients," Theriogenology, 57(1):551 (2002).
Carp, "Effect of diclofenac on implantation and embryonic development in the rat," Eur. J. Obstet. Gynecol. Reprod. Biol., 28(3):273-277 (1998) (Abstract only).
Novaro, "Interaction between uterine PGE and PGF2 alpha production and the nitridergic system during embryonic . . . ," Prostaglandins, 51(6):363-376 (1996) (Abstract only).
Sharif, "AL-3138 antagonizes FP prostanoid receptor-mediated inositol phosphates generation," J. Pharm. Pharmacol., 52(12):1529-1539 (2000) (Abstract only).
Wada, "The benefits of low-dose aspirin therapy in women with impaired uterine perfusion during assisted conception," Hum. Reprod., 9(10):1954-1957 (1994)(Abstract only).
Wollenhaupt, "Control of implantation in rats and sows by peroral administration of prostaglandin synthetase inhibitors," Arch. Exp. Veterarmed, 35(3):471-480 (Abstract only).
Purcell, "Effect of a CIDR insert and flunixin meglumine administered at the time of embryo transfer on pregnancy rate and . . . ," J. Anim. Sci., 82(suppl. 1):103 (2004).
Purcell, "Effect of a CIDR insert and flunixin meglumine administered at the time of embryo transfer on pregnancy rate and . . . ," Theriogenology, 64(4):867-878 (2005).
Scenna, "Influence of a prostaglandin synthesis inhibitor administered at embryo transfer on pregnancy rates . . . ," Prostaglandins & Other Lipid Mediators, 78:38-45 (2005).
Goda, "Abstract 137—Effect of flunixin meglumine in co-culture medium on the development . . . ," Reproduction, Fertility and Development, 17(2):219 (Jan. 1, 2005).
Schrick, "Administration of a prostaglandin inhibitor immediately prior to embryo transfer improves pregnancy rates in cattle . . . ," Theriogenology, 55(suppl.):370 (2001).

*Primary Examiner* — Louise Humphrey
(74) *Attorney, Agent, or Firm* — Howard Eisenberg, Esq.

(57) ABSTRACT

An embryo that is transferred into the uterus of a recipient female is protected from toxic effects of prostaglandin $F_{2\alpha}$ by exposing the embryo, or an oocyte from which the embryo is produced, to a prostaglandin antagonist.

10 Claims, 1 Drawing Sheet

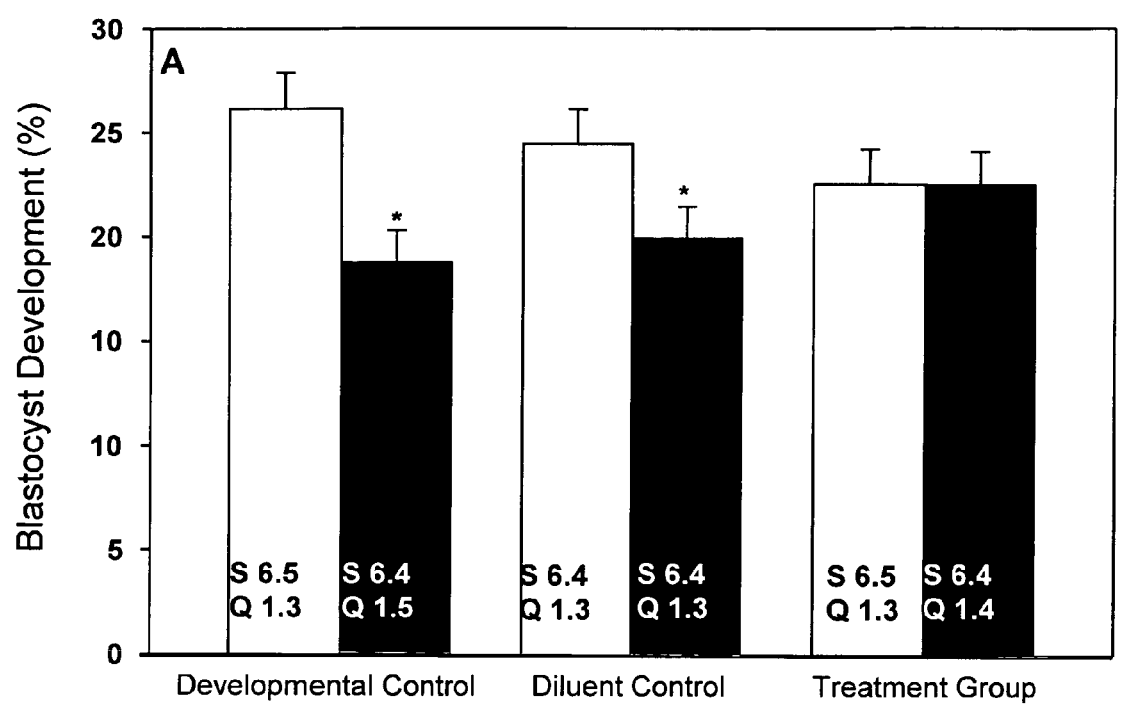

EMBRYO DEVELOPMENT AND SURVIVAL

This application is a continuation-in-part of pending U.S. patent application Ser. No. 11/039,662, which was filed on Jan. 19, 2005, and which issued on Apr. 27, 2010 as U.S. Pat. No. 7,705,197.

It is hereby acknowledged that the U.S. Government has certain rights in the invention described herein, which was supported in part by grants 94-37203-0722 and 99-35208-8402 from USDA-NRICGP.

FIELD OF THE INVENTION

The invention pertains to the field of in vitro fertilization and embryo transfer. In particular, the invention pertains to the field of transferring an in vivo-produced or an in vitro-produced embryo into the uterus of a female human or other mammal.

BACKGROUND OF THE INVENTION

Embryonic loss is a serious problem in the dairy and beef cattle industries, with the majority of these losses occurring during the first week of pregnancy, the period when the non-compacted morula is developing into the hatched blastocyst. Such embryonic losses are typically associated with factors in the oviduct or uterine environment that alter or inhibit embryonic development and/or function of the corpus luteum.

In cattle, these early embryonic losses occur in pregnancies that result from artificial insemination or from natural service. These losses also occur in pregnancies that result from embryo transfer. It is believed that embryonic losses following embryo transfer may be related, at least in part, to manipulation of the reproductive tract with resultant release of an embryotoxin during placement of the embryo in the uterus.

During the embryo transfer procedure in cattle, an embryo is placed in the uterine horn ipsilateral to the corpus luteum. This process requires manipulation of the reproductive tract, including handling of the cervix. It has been reported that such manipulation results in release of prostaglandin $F_{2\alpha}$ ($PGF_{2\alpha}$) into the lumen of the uterus. Wann and Randel, J. Anim. Sci. 68:1389-1394 (1990); Odensvik et al, Acta. Vet. Scand. 34:219-221 (1993). $PGF_{2\alpha}$ is a natural luteolytic substance which is secreted by a female and which, in the absence of pregnancy, ends one estrous cycle in the female animal by destroying the corpus luteum and allows the next cycle to begin. Work in our laboratory has demonstrated that even minimal manipulation of the reproductive tract during embryo transfer results in release of $PGF_{2\alpha}$. Schrick, F N, et al, "Prostaglandin $F_{2\alpha}$ Appears to Directly Influence Early Embryonic Survival in Cattle: Would Administration of Flunixin Meglumine be Beneficial During Embryo Transfer?", in Proceedings of the American Embryo Transfer Association, pp 9-16, Sacramento Calif. (2000).

Several studies have implicated $PGF_{2\alpha}$ as an embryotoxin during the very early time period of pregnancy. Schrick et al, Biol. Reprod., 49:617-621 (1993) reported elevated concentrations of $PGF_{2\alpha}$ in the uterine lumen of postpartum cows compared to normally cycling cows. The increase in uterine $PGF_{2\alpha}$ in these cows was related to the recovery of lower quality embryos compared with cows producing lower levels of $PGF_{2\alpha}$. Seals et al, Prostaglandins 56:377-389 (1998) reported that administration of $PGF_{2\alpha}$ to progestin-supplemented cows between days 5 and 8 of pregnancy caused decreased pregnancy rates compared to saline controls. However, the administration of $PGF_{2\alpha}$ on days 10 to 13 or days 15 to 18 had no effect on pregnancy rates. Further studies by Fazio and Schrick, Biol. Reprod. 56 (Suppl. 1):187 (1997); Hernandez-Fonseca et al, J. Anim. Sci. 75 (Suppl. 1):221 (1997); and Donaldson, Vet. Rec. 118:661-663 (1986) indicate that $PGF_{2\alpha}$ has a detrimental effect on embryonic survival by decreasing the quality of embryos and reducing the developmental rate or ability of an embryo to develop beyond the morula stage.

The deleterious effect of $PGF_{2\alpha}$ on embryonic survival was further established by Schrick et al, Theriogenology 55(1):370 (2001) who reported a study that showed that the administration of a PGF inhibitor to recipient cattle at the time of embryo transfer results in an improvement of pregnancy rates. In this study, the prostaglandin inhibitor flunixin meglamine (BANAMINE, Schering Corp., Kenilworth, N.J., USA) was injected intramuscularly into recipient cattle immediately prior to or after non-surgical transfer of an embryo into the uterine horn ipsilateral to the corpus luteum. Pregnancy rates were significantly higher in cows receiving the prostaglandin inhibitor than in controls.

Thus, the prior art discloses that $PGF_{2\alpha}$ has a deleterious effect on embryonic survival in cattle by reducing the quality of embryos and the developmental rate or ability of an embryo to develop beyond the morula stage. The prior art further discloses that this deleterious effect of $PGF_{2\alpha}$ may be reduced by treatment of a recipient cow with a prostaglandin inhibitor at about the time of embryo transfer, thus effectively reducing the level of $PGF_{2\alpha}$ to which the embryo is exposed.

Similar deleterious effects of $PGF_{2\alpha}$ on embryonic survival and the reduction of this deleterious effect by treatment of the recipient female have been established for mammalian species other than cattle, including humans. See for example, Wollenhaupt, K., and Steger, H, Arch Exp. Veterinarmed., 35(3):471-480 (1981); Waldenstrom, U, et al., Fertility and Sterility, 81(6):1560-1564 (2004); and Rubinstein, M., et al., Fertility and Sterility, 71(5):825-829 (1999).

A significant need exists for ways of reducing embryonic loss following embryo transfer in animals and humans, and especially for ways of reducing such loss without necessitating additional treatment of the recipient (surrogate) female.

BRIEF DESCRIPTION OF THE DRAWINGS

FIG. 1 is a bar graph comparing blastocyst development (%), stage (S), and quality (Q) after maturation of developmentally-competent ova at 38.5° C. or at 41.0° C. in the presence of a $PGF_{2\alpha}$ receptor antagonist. * denotes significance compared to respective control.

DESCRIPTION OF THE INVENTION

It has been unexpectedly discovered that pre-treating an embryo with a prostaglandin antagonist prior to transfer of the embryo to the uterus of a recipient female animal provides a protective benefit to the embryo against the embryotoxic effects due to exposure of the embryo to $PGF_{2\alpha}$ in the uterus of the recipient animal. The invention is useful in embryo transfer in humans and other mammals to provide an increase in percentage of transferable embryos, pregnancies, and live offspring.

In one embodiment, the invention is a method for protecting an embryo to be transferred to the uterus of a recipient female animal. According to this embodiment of the invention, the embryo is exposed to a prostaglandin antagonist before transfer of the embryo to the uterus.

In another embodiment, the invention is a medium for holding, collecting, freezing, culturing, or transferring an embryo, or for maturation of an oocyte that is to be fertilized to produce an embryo, which embryo is to be transferred into the uterus of a recipient female animal. According to this embodiment, the medium contains a prostaglandin antagonist in addition to components necessary for the holding, collecting, culturing, freezing, or transferring or embryos or for maturation of oocytes that are to be fertilized and transferred.

In another embodiment, the invention is a method for performing embryo transfer. According to this embodiment, an embryo is transferred into the uterus of a female animal wherein, prior to the transfer, the embryo has been exposed to a prostaglandin antagonist.

In another embodiment, the invention is a non-human embryo that is protected against the embryotoxic effects due to exposure to $PGF_{2\alpha}$. According to this embodiment, the embryo was exposed to a prostaglandin antagonist during the time that the embryo was situated outside of the uterus of a recipient female animal.

As used herein, the term "exposure" as it pertains to a prostaglandin antagonist and an embryo or an oocyst refers to the exposure of an embryo or oocyst to the prostaglandin antagonist by other than by administering the prostaglandin antagonist to a recipient female with concomitant exposure of an embryo to the prostaglandin antagonist due to circulation of the administered prostaglandin antagonist to the uterus of the female. Such "exposure" by administration to the recipient female animal is not included within the present invention or within the meaning or the term "exposure" as used herein. Exposure of an embryo to a prostaglandin antagonist by infusion of the prostaglandin antagonist into the uterus of a recipient female is included within the present invention and within the meaning of the term "exposure".

As used herein, the term "protect" means to defend an embryo against the direct and/or indirect embryotoxic effects of $PGF_{2\alpha}$ and thus inhibit the death, retardation, or reduction in development of embryos exposed to $PGF_{2\alpha}$. The use of the term "protect" does not mean or imply a guarantee that embryos will not be killed or otherwise harmed when exposed to $PGF_{2\alpha}$ or other factors. Rather, as used herein, this term means that the death rate of embryos due to exposure to $PGF_{2\alpha}$ is reduced or development of embryos is normal in the face of exposure to $PGF_{2\alpha}$ when the embryos are exposed to a prostaglandin receptor antagonist in accordance with the invention as compared with the death rate or abnormal development of embryos exposed to $PGF_{2\alpha}$ but not exposed to the prostaglandin receptor antagonist. Because it is impractical to test any particular embryo to determine if the embryo is "protected", it is conceived that such protection may be determined by historical or statistical means.

As used herein, "placement or transfer of an embryo into the uterus" of a recipient female animal includes such placement or transfer into other portions of the female reproductive system that are utilized in embryo transfer, such as into the oviduct.

As used herein, "prostaglandin antagonist" includes chemical compounds that interfere with the action of prostaglandin, such as aspirin and flunixin meglumine, and chemical compounds that are prostaglandin receptor antagonists which interact with a prostaglandin receptor, such as AL-8810 (Cayman Chemical Co., Ann Arbor Mich.), an 11β-fluoro analog of $PGF_{2\alpha}$, described in Griffen, B. W., Klimko, P., Crider, J. Y., et al., J Pharmacol Exp Ther, 290:1278-1284 (1999). Thus, the term "prostaglandin antagonist" includes both chemical compounds that antagonize the action of prostaglandin itself by any means and those that antagonize the action of prostaglandin by interacting with a prostaglandin receptor. The term "prostaglandin receptor antagonist", as used herein, refers specifically to a chemical compound that interacts with a prostaglandin receptor. Chemical compounds that interfere solely with the synthesis of prostaglandins, such as by interfering with the action of prostaglandin synthetase, but which do not interfere with the action of prostaglandins are not included within the definition of prostaglandin antagonist as used in this specification.

The invention provides a substantial benefit as the various embodiments of the invention provide an increase in the pregnancy rate following embryo transfer. The invention provides a further benefit as the invention reduces or eliminates the need to treat a recipient female human or animal with a prostaglandin antagonist. Treatment of recipient animals is expensive and labor intensive and the results are subject to individual variation. By providing a method for reducing embryonic death due to exposure to $PGF_{2\alpha}$ by treating embryos before transfer, the invention provides a substantial savings in cost and labor, as well as better results, that is higher pregnancy rates, than are attainable by treatment of recipient female animals.

The invention may be practiced in any mammalian species in which embryo transfer or in vitro fertilization is feasible. Although the invention is described herein in reference to cattle (*Bos* species), those skilled in the art will recognize that the invention is applicable to other bovines, such as water buffalo, and other mammals as well. Examples of mammals for which the invention is suitable include humans and other primates such as monkeys and apes, perissodactyla such as horses and rhinoceros, artiodactyla such as pigs, cattle, sheep, goats, camels, llamas, and hippopotamus, carnivora such as dogs, cats, bears, mink, and weasels, pinnipedia such as seals and sea lions, lagomorpha such as rabbits and hares, rodentia such as squirrels, rats, and mice, cetacea such as whales, dolphins, and porpoises, and proboscidea such as elephants.

It has been discovered that $PGF_{2\alpha}$ receptors are present on morula-stage embryos. Although wishing not to be bound by theory, it is conceived that $PGF_{2\alpha}$, acting through such $PGF_{2\alpha}$ receptors, disrupts formation and/or function of junctional complexes between blastomeres, resulting in an interference with continued embryo development. It is further conceived that a prostaglandin antagonist, and preferably a prostaglandin receptor antagonist, when exposed to an embryo in accordance with the invention, inhibits or prevents binding of $PGF_{2\alpha}$ to such receptors, thus preventing or reducing the disruption of the formation and/or function of the junctional complexes and reducing or eliminating this interference with continued embryo development.

The exposure of the embryo to the prostaglandin antagonist may be at any time after collection of an embryo from a donor animal or in vitro fertilization of an oocyte to produce an embryo and before transfer of the embryo to a recipient animal. Thus, the prostaglandin receptor antagonist may be contained in a wash solution to which an embryo is exposed. Preferably, the prostaglandin receptor antagonist is contained in one or more media, such as oocyte maturation media, or collection, culture, or transfer media, in which the embryo is situated between the collection and/or culture and the transfer into the reproductive tract of a recipient animal.

For example, the embryo may be exposed to a prostaglandin antagonist that is contained in one or more of a holding, washing, culture, transfer, manipulation, freezing, or maturation medium. Alternatively, and less preferably, the embryo may be exposed to a prostaglandin antagonist that is contained within a fluid with which the embryo or oocyte is bathed or washed before or after placement of the embryo into a medium or transfer of the embryo into the recipient female.

The concentration of the prostaglandin antagonist to which the embryo or oocyte is exposed and the time during which the embryo or oocyte is exposed to the prostaglandin antagonist may vary depending on several variables, including the nature of the medium or wash fluid in which the prostaglandin receptor antagonist is contained, the particular prostaglandin receptor antagonist to which the embryo is exposed, and whether the embryo or oocyte is immersed in the fluid or medium or alternatively if the medium or fluid flows over the embryo or oocyte.

The prostaglandin antagonist that is useful for the method of the invention is a chemical compound that inhibits the action of a prostaglandin, such as by interfering with the binding of the prostaglandin to a prostaglandin receptor. Thus, the prostaglandin antagonist that is suitable for the invention may be a general prostaglandin antagonist, such as flunixin meglamine, aspirin, or omega-3 fatty acids.

In a preferred embodiment, the prostaglandin antagonist is a chemical compound that selectively inhibits $PGF_{2\alpha}$, and preferably does not substantially interfere with the activity of Prostaglandin E (PGE). PGE is a smooth muscle stimulator which has opposite effects from those of $PGF_{2\alpha}$ on the corpus luteum and embryo. In contrast to $PGF_{2\alpha}$, PGE has antiluteolytic action in that it inhibits the luteolysis that is induced by $PGF_{2\alpha}$.

An example of a selective prostaglandin receptor antagonist that is useful for the invention is AL-8810 (11β-fluoro-15-epi-15-indanyl-tetranor $PGF_{2\alpha}$) (Cayman Chemical Co., Ann Arbor Mich.), an 11β-fluoro analog of $PGF_{2\alpha}$. Examples of other prostaglandin receptor antagonists include AL-3138 (11-deoxy-16-fluoro $PGF_{2\alpha}$), THG113 (see, Peri K G, et al, Semin Perinatol. 26(6):389-397 (2002), and phloretin. Other selective $PGF_{2\alpha}$ antagonists and $PGF_{2\alpha}$ receptor antagonists, known and yet to be discovered, are also suitable for the invention.

In accordance with a preferred embodiment of the method of the invention for protecting an embryo to be transferred to the uterus of a recipient female animal, an embryo that is to be transferred into the uterus of a recipient female animal is exposed to the prostaglandin receptor antagonist at a time that is during and/or after the embryo is collected from a donor animal and before the embryo is transferred into the recipient female. The embryo may be one that is pre-compacted, compacted, or post-compacted such as a blastocyst. Typically, the exposure of the embryo to the prostaglandin antagonist is by holding, washing, culturing, freezing, or transferring the embryo in a culture medium in which is incorporated one or more prostaglandin antagonists. The prostaglandin antagonist is preferably a selective blocker of $PGF_{2\alpha}$. The embryo is exposed to the prostaglandin antagonist for a time and at a concentration that is effective to protect the embryo, completely or partially, from the embryotoxic effects of $PGF_{2\alpha}$.

In accordance with a preferred embodiment of the method of the invention for performing embryo transfer, an embryo to be transferred is exposed to a prostaglandin antagonist at a time between, or during, collection of the embryo from a donor animal or culture of an oocyte in vitro to produce an embryo and transfer of the embryo to a recipient animal, and the embryo is then transferred into the uterus of the recipient animal. Typically, the exposure of the embryo to the prostaglandin receptor antagonist is in vitro by holding, culturing, freezing, or transferring the embryo in a collection or culture medium in which is incorporated one or more prostaglandin antagonists. The prostaglandin antagonist is preferably a selective blocker of $PGF_{2\alpha}$. The embryo is exposed to the prostaglandin antagonist for a time and at a concentration that is effective to protect the embryo, completely or partially, from the embryotoxic effects of $PGF_{2\alpha}$. Any method of collecting an embryo from a donor animal, any method of fertilizing an oocyte to produce an embryo, any method of preparing an embryo for transfer into the uterus of a recipient animal, and any method of transferring an embryo into the uterus of a recipient animal, whether such methods are presently known or are later discovered, are suitable for this method of the invention.

In accordance with the medium of the invention, the medium may be, for example, for maturation of an oocyte that is to be fertilized and transferred into the uterus of a recipient female animal, or for holding, collecting, culturing, freezing, treating, or transferring an embryo that is to be transferred into the uterus of a recipient female animal. The medium of the invention contains components necessary for its utilization as such a medium and, in addition, contains a prostaglandin antagonist at a concentration that is effective to protect an embryo that is situated in the medium from the embryotoxic effect of $PGF_{2\alpha}$ that may be encountered following transfer of the embryo into the uterus of the recipient female.

In accordance with the non-human embryo of the invention, the embryo is a mammalian embryo that is situated inside or outside of a female animal and is exposed, or has been exposed, to a prostaglandin antagonist such that the embryo is protected against embryotoxic effects of $PGF_{2\alpha}$ that may be encountered upon transfer of the embryo into the uterus of a female animal.

The invention is further described by the following non-limiting examples.

Example 1

Evaluation of Direct Effects of $PGF_{2\alpha}$ on Embryos

Because studies in the prior art regarding $PGF_{2\alpha}$ and embryonic development were performed in vivo, the possibility exists that the embryonic effects of $PGF_{2\alpha}$ that were reported were due to an indirect effect of $PGF_{2\alpha}$ rather than a direct effect on the embryos. Therefore, studies are performed to determine if direct effects of $PGF_{2\alpha}$ occur on embryonic development during culture of pre-compacted (in vitro-produced) or compacted (in vivo-produced) embryos.

Example 1.a

Pre-Compacted Embryos

Embryos are produced by a modified protocol for in vitro production of embryos described by Edwards and Hansen, Biol. Reprod. 55:340-346 (1996). Pre-compacted 16- to 32-cell stage embryos are rapidly washed in KSOM media (Biggers, J. D. 1991. J. Reprod. Fertil. 91:543) supplemented with polyvinyl alcohol (PVA) 3 mg/ml (0.3%). The embryos are evaluated for quality (normal shape, defined blastomeres, extruded blastomeres, cytoplasmic fragmentation, even cytoplasm), are evenly sorted in four groups (formed by embryos of good quality), are transferred to experimental treatments in a 4-well plate as described below, and are returned to the incubator (5.5% $CO_2$, 7% $O_2$, and 87.5% $N_2$ at 38.5° C.). Embryos remain in each treatment for 4 additional days. Embryo development is assessed using IETS (International Embryo Transfer Society) guidelines for classification of bovine embryos.

Dilutions (i.e., treatments) of $PGF_{2\alpha}$ (Cayman Chemical Co.; Ann Arbor, Mich.) are prepared to obtain 0, 1, 10 and 100 ng/mL. Treatments are placed in each well of a 4-well plate (500 μL/well) and equilibrated in the incubator (5.5% $CO_2$, 7% $O_2$, and 87.5% $N_2$ at 38.5° C.) for at least 5 h prior to embryo placement. For each replicate, two media samples from each treatment are collected to determine concentrations of $PGF_{2\alpha}$ by radioimmunoassay (RIA). The first sample is collected on the day in which treatments begin (approximately day 5 of culture) and the second sample obtained after determination of blastocyst development (day 9 of culture).

A total of 7 replicates are utilized. In each replicate, embryos at 16- to 32-cell stage are placed in KSOM media supplemented with 0.3% PVA and receive one of the following culture treatments: 1) control (n=168); 2) 1 ng/mL $PGF_{2\alpha}$ (n=143); 3) 10 ng/mL $PGF_{2\alpha}$ (n=168); 4) 100 ng/mL $PGF_{2\alpha}$ (n=136), and 5) 5 ng/mL $PGE_2$ (n=62). Prostaglandin $E_2$ is thought to be a "beneficial" prostaglandin during embryo development (Biggers et al. Biol. Reprod. 19:519-533. (1978)). Therefore, embryos cultured in media with addition of 5 ng/mL of $PGE_2$ are considered to be a positive control group (Gurevich et al., Reprod. Fertil. Dev. 5:281-283 (1993)) and to ascertain if any effects are associated simply with prostaglandins, per se.

Data are analyzed to test for blastocyst development and hatching rates using an incomplete block design and a randomized block design, respectively. Analysis of variance is performed using mixed models (SAS 8.02, SAS Institute Inc., Cary, N.C.) and contrasts are tested to identify differences across levels of $PGF_{2\alpha}$ on embryonic development. Analyses are then validated with Chi-square analysis (SAS 8.02, SAS Institute Inc., Cary, N.C.).

Results indicate that culture of 16- to 32-cell pre-compacted (in vitro-produced) embryos with 1, 10 or 100 ng/mL of $PGF_{2\alpha}$ in the medium reduced blastocyst development when compared to control (P=0.002). Furthermore, blastocyst development does not differ between control and $PGE_2$ treatments (P>0.10). Thus, addition of $PGF_{2\alpha}$ to culture medium has a direct negative effect on development of 16- to 32-cell in vitro-produced embryos to blastocyst.

Example 1.b

Compacted Embryos

In vivo-derived glycerol-frozen morula-stage bovine embryos are thawed utilizing a three-step glycerol removal procedure. After washing, embryos are allowed to regain normal morphology for 30 min in Vigro holding medium and are sorted by stage of development and quality according with the IETS guidelines for classification of bovine embryos. For this study, a total of 4 replicates are used.

Schrick, et al, Biol. Reprod. 49:617-621 (1993) reported 0.64 ng/mL of $PGF_{2\alpha}$ in flush media from short cycle cows and a negative association of $PGF_{2\alpha}$ concentration with embryo quality. Based on these findings, concentrations of 0 (control, KSOM-PVA), 0.1, 1, and 10 ng/mL of $PGF_{2\alpha}$ in culture medium are selected as treatments. Each treatment is placed in a different well of a 4-well plate (500 µL/well) and then maintained in the incubator (5.5% $CO_2$, 7% $O_2$, and 87.5% $N_2$ at 38.5° C.) for at least 5 h before placement of embryos to allow equilibration of medium. At the same time, media samples from each treatment are collected and stored at -20 C.° for determination of $PGF_{2\alpha}$ concentrations by radioimmunoassay (RIA).

Morula embryos (Stage 4) of quality grade 1, 2 or 3 are rapidly washed four times in KSOM-PVA and randomly assigned to one of four treatments: 1) control (n=110); 2) 0.1 ng/mL $PGF_{2\alpha}$ (n=108); 3) 1 ng/mL $PGF_{2\alpha}$ (n=109), 4) 10 ng/mL $PGF_{2\alpha}$ (n=109) and are placed in the incubator (5.5% $CO_2$, 7% $O_2$, and 87.5% $N_2$ at 38.5° C.). After culturing embryos for 24 h in their respective treatment, embryos are washed and placed in KSOM-BSA without $PGF_{2\alpha}$ for an additional 48 h. Evaluation of embryo development using IETS guidelines for classification of bovine embryos is performed by experienced technicians uninformed of treatments. Data are analyzed as in Example 1.a.

Results of this study show that development of compacted (in vivo-derived) morula stage embryos, at least two stages beyond morula utilizing IETS guidelines for development, does not differ between treatments (P>0.10). However, culture of embryos in 0.1, 1, or 10 ng/mL of $PGF_{2\alpha}$ for 24 h shows decreased hatching rates when compared to control (P=0.05).

Example 2

Presence of $PGF_{2\alpha}$ Receptor Transcripts in Morula-Stage Embryos

Embryos are produced in vitro as described above. On day 6 of embryonic development, morula stage embryos are transferred to an "X" plate containing pre-warmed PBS supplemented with 0.1% PVA (polyvinyl alcohol, Sigma; St. Louis, Mo.). Embryos are washed twice in the same solution and then placed in a 1.5 mL RNAse-free eppendorf tube containing 50 µL of RNA later solution (Ambion Inc., Austin, Tex.). Pools of approximately 20 embryos in RNA later are kept at 4° C. overnight and stored at -80° C. until RNA isolation and further processing.

The Absolutely RNA Nanoprep Kit (Stratagene, La Jolla, Calif.) is used to isolate highly pure total RNA from bovine embryos as described by the manufacturer's instructions. In order to decrease the viscosity of RNA later, 70 µl of nuclease free water are added to each sample. Samples are spun at 7,000 g for 5 min and the supernatant removed. Embryos are then lysed by addition of a combination of β-mercaptoethanol and lysis buffer. Following cell lysis, the sample is transferred to a nano-spin cup where the RNA binds to a silica-based fiber matrix. Contaminant DNA is removed by a Dnase digestion step using Dnase I enzyme. Then, a series of high and low salt buffer washes removes Dnase I enzyme and other proteins. Lastly, highly pure RNA is eluted from the fiber matrix with 10 µL of a low-ionic-strength buffer. Elution samples are kept at -80° C. until use.

As a positive control, total RNA from bovine tongue epithelium is isolated using Trizol Reagent (Invitrogen, Carlsbad, Calif.). Epithelial cells are obtained from a fresh tongue by slicing off the epithelium in sections less than 0.5 cm thick and placing them into RNA later solution. Tongue samples are then placed at 4° C. overnight and kept at -80° C. until use. To isolate RNA, 100 mg of tongue epithelium are placed in a 17×100 mm polypropylene tube containing 1 mL of Trizol and tissue samples are homogenized using a power homogenizer (Tekmar's Tissumizer, Tekmar Co., Cincinnati, Ohio). Homogenized samples are incubated for 5 min at room temperature followed by the addition of 0.2 mL of chloroform. Tubes are vigorously shaken by hand for 15 sec and incubated at room temperature for 15 min. Samples are then centrifuged at 12,000 g for 10 min at 4° C. After centrifugation, the aqueous phase is transferred to a fresh tube, where RNA is precipitated by the addition of 0.5 mL isopropyl alcohol and incubation of the samples at room temperature for 15 min. Samples are centrifuged at 12,000 g for 10 min at 4° C., the supernatant is removed and the resulting RNA pellet is washed once using 75% ethanol. Finally, the RNA pellet is air-dried for 5 min, dissolved in 50 µl of nuclease free water and stored at -80° C. until use.

In each of 4 replicates, isolated RNA from 20 compacted morula embryos and 180 ng total RNA from bovine tongue epithelium are reverse transcribed into cDNA in a total volume of 25 µl. The reaction mixture consists of 1X RT buffer, 5 mM $MgCl_2$, 1 mM of each dNTP, 0.25 nM random hexamers, 20 iu RNase inhibitor, and 100 iu murine leukemia virus reverse transcriptase (MMLV-RT). All reagents used for the RT reaction are purchased from Promega (Madison, Wis.). The RT reaction is carried out at 25° C. for 10 min, and then at 42° C. for 1 h followed by a denaturation step at 99° C. for 5 min and flash cooling to 4° C. As negative controls, tubes are always prepared in which reverse transcriptase is omitted during the RT reaction.

Presence of $PGF_{2\alpha}$ receptor is analyzed by Real Time PCR. Using isolated RNA from in vitro-derived morula-stage embryos, three Real Time PCR replicates are conducted to determine $PGF_{2\alpha}$ receptor transcripts. In each replicate, 10 equivalent embryo (1 equivalent embryo=percentage of the volume from the RT reaction employing one embryo in a defined volume) per tube are utilized to determine the expression of each transcript. Polymerase chain reaction is performed using the iCycler iQ™ Real-Time PCR detection system (Bio-Rad, Hercules, Calif.) and the iQ™ SYBR Green Supermix (Bio-Rad, Hercules, Calif.). The PCR reaction mixture contains of 25 µl 1X iQ Supermix (100 mM KCl, 40 mM Tris-HCl, pH 8.4, 0.4 mM of each dNTP, iTaq DNA Polymerase 50 units/ml, 6 mM MgCl2, SYBR Green I, 20 nM fluorescein, and stabilizers), 1 µM concentration of forward primer, 1 µM concentration of reverse primer, 4.5 nuclease free water, 10 µl of template from RT reaction, and 0.5 µl of fluorescein. Negative control for each primer set consists of PCR reaction mixture without the inclusion of cDNA.

Histone $A_2$ amplification is used as a standard control of the Real Time PCR. The Real Time PCR protocol includes an initial step of 95° C. for 15 min followed by 40 cycles of 95° C. for 15 sec, 55° C. for 30 sec, and 72° C. for 30 sec. Fluorescence data are acquired during the elongation step. The melting temperatures of $PGF_{2\alpha}$ receptor and histone $A_2$ genes are 84° C. and 90° C., respectively. Therefore, melting curve analysis shows a sharp peak at the expected Tm of the various products. The melting protocol is performed by holding temperature at 45° C. for 60 sec and then heating from 45 to 94° C., holding at each temperature for 5 sec while monitoring fluorescence. Product identity is confirmed by ethidium-bromide-stained 2% agarose gel electrophoresis in 1X TBE buffer (90 mM Tris, 90 mM borate, 2 mM EDTA, pH 8.3; FIGS. 1 and 2). In addition, amplicon identity of $PGF_{2\alpha}$ receptor is confirmed by DNA sequencing of Real Time PCR fragments.

The RT-RT-PCR analysis demonstrates that $PGF_{2\alpha}$ transcripts are present in embryos during early development. Positive control $PGF_{2\alpha}$ transcripts from bovine tongue epithelium are readily apparent on ethidium-bromide-stained agarose gel and from in vitro produced bovine embryos.

Example 3

Effect of a $PGF_{2\alpha}$ Receptor Antagonist on In Vitro Development of Embryos Pre-compacted 16- to 32-cell stage bovine embryos (day 4 post fertilization) are washed in KSOM-PVA and divided into four groups, each of which is cultured for 48 hours in KSOM-PVA containing one of the following: (1) 1000 nM AL-8810, n=95 (AL-8810 group); (2) 1 ng/ml PGF, n=91 (PGF group); (3) 1000 nM AL-8810+1 ng/ml PGF, n=90 (AL-8810+PGF group); or (4) KSOM-PVA without AL-8810 or PGF, n=84 (Control group).

Following the 48 hour culture, embryos from each group are placed in HEPES-TALP and embryonic development is assessed by a technician who is uninformed of the treatments of the embryos in each group. Embryos from each treatment group are washed in KSOM-PVA and transferred to a 4-well plate with KSOM-PVA for further culture until day 8 post fertilization, when embryonic development is again assessed.

Data indicates that addition of PGF on days 4 to 6 decreases the percentage of embryos reaching blastocyst stage on day 8. However, addition of AL-8810 to the culture medium decreases the negative effects of PGF on embryonic development and restores embryonic development to values similar to those of the Control group.

Example 4

Dose Response Study

Pre-compacted 16- to 32-cell stage bovine embryos (day 4 post fertilization) are washed in HEPES-TALP and divided into four groups, each of which is transferred to treatments in a 4-well plate containing 500 ul of KSOM-PVA (0.3%) and returned to the incubator for 96 hours. Incubation conditions are 5.5% $CO_2$, 7% $O_2$, and 87.5% $N_2$ at 38.5° C. The four groups are as follows: (1) KSOM-PVA+AL-8810 at 1000 nM, n=93 (High AL-8810 group); (2) KSOM-PVA+AL-8810 at 500 nM, n=95 (Medium AL-8810 group); (3) KSOM-PVA+AL-8810 at 250 nM, n=93 (Low AL-8810 group); and (4) KSOM-PVA with an equivalent volume of DMSO (dimethylsulfoxide) as used for the first three groups, n=95 (Control group). Following the 96 hour incubation, embryos from each group are placed in HEPES-TALP and embryonic development is assessed by a technician who is uninformed of the treatments of the embryos in each group.

Data indicates that addition of three different concentrations of the prostaglandin inhibitor AL-8810 to culture medium on days 5 through 8 after fertilization does not decrease or increase early embryonic development of pre-compacted embryos when compared to a control group. When only the High AL-8810 and the Control group are analyzed, there is a significant difference in these two groups (60.3%+/−3.9% (High AL-8810 group) vs. 49.9+/−3.9% (Control group); p<0.05).

Example 5

Pre-treatment of Embryos Before Transfer

Approximately 100 embryo recoveries are performed on day 7 after estrus in beef and dairy cows (lactating and dry). Cows are superovulated (Folltropin) and embryos recovered, evaluated, and frozen (1.5 M Ethylene Glycol; EG) as previously reported (Schrick et al., Biol. Reprod. 49:617-621 (1993)). Half of the embryo recoveries occur utilizing 1 L of each of the following alternative media preparations: 1) Embryo recovery (flush) media (CON, n=50 recoveries; Dulbecco's PBS+1% FCS; GibcoBRL, Cat.#21300-025; Grand Island, N.Y.) or 2) Embryo recovery (flush) media+AL-8810 (TRT, n=50 recoveries; 430 nM of AL-8810).

Following filtering, embryo dishes are searched, embryos removed (placed in Vigro), and evaluated for quality and development (IETS guidelines). One half of recovered embryos of acceptable development and quality (1-3; IETS) from each flush are frozen individually for direct transfer using 1.5 M EG supplemented with 1) Vigro (F/T Control, n=250 embryos) or 2) Vigro+AL-8810 (F/T Treated, n=250 embryos). Embryos are placed in their respective F/T media treatment for a period of less than 5-10 min following evaluation and before placement in the freezing unit (BioCool controlled rate freezer; FTS Systems, Inc.; Warren, Mich.). Following placement into labeled (Embryo ID) 0.25 mL straws, embryos are frozen (seeding −6° C.; freezing rate: −0.5° C./min) to −32° C., and plunged into a liquid nitrogen storage tank. Embryos remain in the tank for no less than two weeks before transfer to acceptable recipient animals.

Over a two year period, recipient animals (dairy and beef cows and heifers; n=500) have estrus synchronized utilizing GnRH/CIDR/Estrumate protocol consisting of administration of 100 ug GnRH (Cysterolin; Merial) and CIDR (intravaginal progesterone releasing device; Pfizer) insertion on day 0, CIDR removal and injection of 2 mL Estrumate (Schering-Plough Animal Health) on day 7, and estrous detection (twice daily) from days 8 through 12. Seven days after detection of a synchronized estrus, animals are placed in cattle handling facility, blood collected via tail vein for progesterone concentrations (P4 conc. determined as described by Seals et al., 1998), corpus luteum (CL) palpated for acceptability and location, and the embryo placed (embryo transfer, ET) in the upper one half of the uterine horn ipsilateral to the CL (Schrick et al., 1993). Embryos used for ET are thawed (10 sec air thaw; 30 sec in 25° C. water bath), straw labeling (embryo ID) information recorded, and recipient ID collected.

Embryos recovered from beef cattle donors are placed in beef recipients (Angus) and embryos from dairy cattle donors are placed only in dairy recipients (Holstein). On days 21-28, recipients are scanned using transrectal ultrasonography for determination of pregnancy. All animals are palpated rectally 90-150 days after transfer for final pregnancy call. At calving, calves are evaluated for health and gross abnormalities, weighed, identification tag inserted, and sex recorded.

The results of this study establish that the addition of a $PGF_{2\alpha}$ antagonist to media in which an embryo resides, such as the embryo recovery and/or freezing/transfer (F/T) media, increases pregnancy rates of embryos placed in acceptable recipients. No abnormalities are observed in the calves resulting from the pregnancies.

Example 6

Treatment of Oocytes with a $PGF_{2\alpha}$ Antagonist

Studies were performed to establish that the exposure of oocytes to a $PGF_{2\alpha}$ antagonist would aid in the development of maturing oocytes by protecting them against the detrimental effects of $PGF_{2\alpha}$. Previous research had established that cumulus-oocyte-complexes (COC) produce $PGF_{2\alpha}$, that both oocytes and cumulus cells have $PGF_{2\alpha}$ receptors, that addition of $PGF_{2\alpha}$ to oocytes above what they normally produce decreases blastocyst development of later-fertilized oocytes, and that reproductive tissues that were heat stressed by exposure to elevated temperatures produced increased levels of $PGF_{2\alpha}$. Therefore, the study was designed to assess development of heat-stressed ova matured in the absence or presence of a $PGF_{2\alpha}$ antagonist.

In a first study, bovine cumulus-oocyte-complexes were divided into three groups. Each of the three groups were matured for 24 hours under heat-stress conditions at 41.0° C. for 12 hours, followed by 38.5° C. for the remaining 12 hours. A first group, referred to as the development control group, was matured utilizing a standard maturation medium. A second group, referred to as the diluent control group, was matured under the same conditions utilizing the same standard maturation medium to which was added a diluent DMSO (dimethyl sulfoxide). A third group, referred to as the treatment group, was matured under the same conditions utilizing the same standard maturation medium to which was added the $PGF_{2\alpha}$ antagonist AL-8810 at a concentration of 250, 400, or 1000 nM. To prepare the diluent control, DMSO was added to the OMM to yield the same concentration as would be contained in the $PGF_{2\alpha}$ antagonist dose being tested (0.0025, 0.004 and 0.01% v/v final concentration for the 250, 400 and 1000 nM doses, respectively). The generalized linear mixed models (GLIMMIX) procedure of SAS version 9.1 (SAS Institute; Cary, N.C.; 2003) was used to perform analyses. Data are presented as least square means±the standard error of the mean. Fixed effects in the statistical model to evaluate the development of heat-stressed ova matured in the presence of a $PGF_{2\alpha}$ receptor antagonist included maturation temperature (38.5 or 41.0° C.), FPr-A (250, 400 and 1000 nM) and the respective interaction.

In order to have a more precise test of hypothesis (oocyte maturation in the presence of a $PGF_{2\alpha}$ receptor antagonist, when one would expect ova to be exposed to excessive amounts of $PGF_{2\alpha}$, may improve development), only those experimental replicates whereby a stressor (elevated temperature) decreased blastocyst development greater than 10% compared to controls (n=14 replicates) were included in the statistical analysis. When this was done, a significant maturation temperature×$PGF_{2\alpha}$ antagonist interaction was noted (P=0.05).

As shown in FIG. 1, culture of COC at 41.0° C. for the first 12 h of in-vitro maturation reduced blastocyst development in both the developmental and diluent controls. However, when COC were matured under identical conditions in the presence of a $PGF_{2\alpha}$ antagonist, the effect of heat stress to reduce blastocyst development was no longer observed and in fact, development was comparable to those ova matured at 38.5° C.

In a second study, bovine oocytes were obtained from ovaries of slaughtered cows. Oocytes that were developmentally challenged (development of oocyte to blastocyst less than 20%) were included in the study. The oocytes were matured for 24 hours in a standard maturation medium that either contained the $PGF_{2\alpha}$ antagonist AL-8810 (treatment group) or that lacked the $PGF_{2\alpha}$ antagonist (control group) and were then fertilized. Oocytes were observed on day 3 for the presence of cleavage and on day 9 for the presence of blastocyst development. The percentage of oocytes in that underwent cleavage and that developed into blastocysts was determined. Results are shown in Table 1.

TABLE 1

|  | COC (n) | Cleaved (%) | 2-cell (%) | 4-cell (%) | 8 to 16-cell (%) | Blastocyst/PZ (%) |
| --- | --- | --- | --- | --- | --- | --- |
| Control | 780 | 57.1 | 9.6 | 17.1 | 72.7 | 13.1 |
| Treatment | 914 | 60.4 | 7.2 | 15.2 | 76.7 | 17.7 |

As shown in Table 1, a statistically significant higher percentage of developmentally challenged oocytes that were treated with the $PGF_{2\alpha}$ antagonist prior to fertilization cleaved, and of those that cleaved, a higher percentage were observed to 8 to 16-cell embryos than those oocytes that were not treated with the $PGF_{2\alpha}$ antagonist. In addition, a statistically significant higher percentage of oocytes that were treated with the $PGF_{2\alpha}$ antagonist developed into blastocysts compared to oocytes that were not treated with the $PGF_{2\alpha}$ antagonist. When stage and development of blastocysts were evaluated from the two groups, no difference was noted. This lack of difference establishes that the $PGF_{2\alpha}$ antagonist does not exert a deleterious or toxic effect on the oocytes or developing embryos.

The results of these studies establish that exposure of oocytes to a $PGF_{2\alpha}$ antagonist increases the efficiency of procedures utilized for in vitro production of embryos.

Further modifications, uses, and applications of the invention described herein will be apparent to those skilled in the art. It is intended that such modifications be encompassed in the claims that follow.

The invention claimed is:

1. A method for protecting a mammalian oocyte that is susceptible to toxic effects of prostaglandin F2α from said toxic effects of prostaglandin F2α comprising exposing the oocyte to a chemical compound that is a prostaglandin F2α antagonist in an amount and for a time sufficient to protect the oocyte from the toxic effects of prostaglandin F2α.

2. The method of claim 1 wherein the oocyte is exposed to the chemical compound during the time the oocyte is situated in a medium containing the prostaglandin F2α antagonist.

3. The method of claim 1 wherein the F2α prostaglandin antagonist is a prostaglandin receptor antagonist.

4. The method of claim 1 wherein the oocyte is a bovine oocyte.

5. A method for performing embryo transfer comprising obtaining a mammalian embryo to be transferred into the uterus of a recipient female animal, wherein the embryo has been produced from an oocyte that has been exposed to a chemical compound that is a prostaglandin F2α antagonist in an amount and for a time sufficient to protect the oocyte from toxic effects of prostaglandin F2α, and then transferring the embryo into the uterus of a recipient female animal of the same species as the embryo.

6. The method of claim 5 wherein the oocyte was exposed to the chemical compound during the time the oocyte was situated in a medium containing the prostaglandin F2α antagonist.

7. The method of claim 5 wherein the embryo is a bovine embryo.

8. The method of claim 5 wherein the embryo is selected from the group consisting of a pre-compacted embryo, a compacted embryo, and a post-compacted embryo.

9. The method of claim 5 wherein the embryo is a blastocyst.

10. The method of claim 5 wherein the prostaglandin F2α antagonist is a prostaglandin F2α receptor antagonist.

* * * * *

UNITED STATES PATENT AND TRADEMARK OFFICE
Certificate

Patent No. 8,715,155 B2                                                                  Patented: May 6, 2014

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: F. Neal Schrick, Knoxville, TN (US); and Lannett Edwards, Knoxville, TN (US).

Signed and Sealed this Fifteenth Day of July 2014.

ZACHARIAH LUCAS
*Supervisory Patent Examiner*
Art Unit 1648
Technology Center 1600